United States Patent [19]

Tamura et al.

[11] 4,096,268
[45] Jun. 20, 1978

[54] 1-METHYL-1,2,5,6-TETRAHYDROPYRIDINE-3-CARBOXYLIC ACID ESTERS AND A METHOD OF USE FOR COMBATING INSECTS OR ACARIDS

[75] Inventors: Saburo Tamura; Junichi Saito; Akio Kudamatsu; Yoji Ishino; Toshio Goto, all of Tokyo, Japan

[73] Assignee: Bayer Aktiengesellschaft, Leverkusen, Germany

[21] Appl. No.: 712,579

[22] Filed: Aug. 9, 1976

Related U.S. Application Data

[63] Continuation of Ser. No. 628,878, Nov. 5, 1975, abandoned.

[30] Foreign Application Priority Data

Nov. 14, 1974 Japan .................................. 49-130513

[51] Int. Cl.² ...................... A01N 9/22; C07D 213/55
[52] U.S. Cl. ............................... 424/266; 260/295.5 R
[58] Field of Search .................... 260/295.5 R, 295 R; 424/266

[56] References Cited

PUBLICATIONS

Mutschler et al., Chem. Abstracts, vol. 79, (9), 53, 147r, Sep. 1973. Jun.

Chem. Abstracts, vol. 76, Chem. Substance Index (P-Z) pp. 3110-3111, June, 1972.
Preobrazhenskii et al., Chem. Abstracts, vol. 52 (10) 9162c-i, (May, 1958).
Chem. Abstracts, vol. 80, Chem. Substance Index (P-Z) pp. 3378-3379, Jun. 1974.
Tsukasa, Chem. Abstracts, vol. 80 (23), 128, 096e, Jun. 1974.

Primary Examiner—Alan L. Rotman
Attorney, Agent, or Firm—Burgess, Dinklage & Sprung

[57] ABSTRACT

1-Methyl-1,2,5,6-tetrahydropyridine-3-carboxylic acid esters of the formula

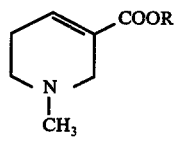

wherein R stands for an alkyl group having 3 to 6 carbon atoms, a cycloalkyl group, an alkenyl group having 2 to 6 carbon atoms or an alkynyl group having 2 to 6 carbon atoms, or a salt thereof.

These compounds plus that where R is ethyl are used in combatting insects and acarids.

1 Claim, No Drawings

1-METHYL-1,2,5,6-TETRAHYDROPYRIDINE-3-CARBOXYLIC ACID ESTERS AND A METHOD OF USE FOR COMBATING INSECTS OR ACARIDS

This is a continuation of application Ser. No. 628,878, filed Nov. 5, 1975, now abandoned.

The present invention relates to and has for its objects the provision of particular new 1-methyl-1,2,5,6-tetrahydropyridine-3-carboxylic acid esters which possess insecticidal and acaricidal properties, active compositions in the form of mixtures of such compounds with solid and liquid dispersible carrier vehicles, and methods for producing such compounds and for using such compounds plus one other in a new way especially for combatting pests, e.g. insects and acarids, with other and further objects becoming apparent from a study of the within specification and accompanying examples.

Chemische Berichte, Volume 21 (1888) page 3404, describes the extraction and fractionation of arecholine of the formula

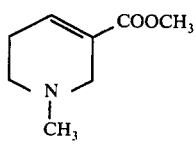

and the preparation of salts thereof.

U.S. Pat. No. 2,506,458 issued in 1950 discloses the preparation of arecholine of the above formula and arecaidine ethyl ester of the formula

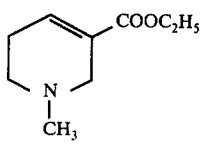

making mention of the usefulness of these compounds in the veterinary field.

The above-mentioned arecholine is a naturally occurring alkaloid contained in the fruit of the betel nut, being known as a parasympathetic nerve affecting substance in the field of medicine and also used as a vermicide for livestock.

However, arecholine has never been used as an insecticidal agent and no effectiveness of it for use as an insecticidal agent is either stated or even suggested in any of the literature.

This invention is based on the surprising discovery that tetrahydropyridinecarboxylic acid esters defined below have considerable insecticidal and acaricidal effects, much greater than that of arecholine which is a naturally occurring alkaloid.

In practice, the insecticidal agents which have actually been used have generally been such inorganic compounds as arsenical compounds or such organic synthetic insecticidal agents as certain organic phosphorus compounds, carbamate compounds and organic chlorine compounds.

However, many of the organic synthetic insecticidal agents of which widespread use has been made in recent years cause problems of acute toxicity, chronic toxicity and residual toxicity; for instance, some remain and build up in the soil, or migrate into the actual crop, and may pose toxicity problems in the food for humans and for livestock, or may pass into rivers and injure fish and shellfish, or cause the transmission of toxicity through the food chain to more remote consumers. Thus such compounds contribute to environmental pollution. Many such compounds have had to be restricted or entirely prohibited in use as in the case of lead arsenate, BHC and DDT.

The repeated use of the same type of chemicals in successive years gives rise to different problems, such as pests gaining resistance thereto, reducing the effictiveness of the pesticides.

On the one hand, natural insecticidal agents have a narrow insecticidal spectrum and a short residual effect, though quick in taking effect. They are often readily decomposed by the sunlight and air and are thus deprived of insecticidal effect, so that they do not remain in the soil or crop and do little damage to the crop.

When they are actually used, it becomes necessary in order to make certain of their insecticidal effect either to use synergists concurrently with them or to increase the amount applied, there being many problems posed from the view-points of insecticidal effect and economy. Thus, there are not many of them that can compare favorably with synthetic agricultural chemicals.

Under these circumstances, the need for the advent of alternative agricultural chemicals with low toxicity is rapidly more and more felt.

The present inventors repeatedly engaged themselves in the examination and study of the working characteristics of natural insecticidal agents, in which they took notice of the action and structure of arecholine which is a naturally occurring alkaloid and synthesized its derivatives, finding as a result that tetrahydropyridinecarboxylic acid esters of the general formula (I) and their salts possess an excellent insecticidal and acaricidal effect, having a peculiar selectivity in action and being free from phytotoxicity to the crop, and can therefore be used with safety.

Further, there is an advantage in that the compounds of the invention, which have an altogether different working mechanism from the conventional chemicals, have a very high insecticidal and acaricidal effect against various types of pests which have gained resistance to chemicals as a result of the same types of chemicals being used in successive years and in that they are low in toxicity to warm-blooded animals, which makes it possible to use with safety.

The invention provides novel compounds which are tetrahydropyridinecarboxylic acid esters of the general formula:

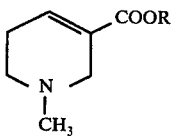

(I)

wherein R stands for an alkyl group having 3 to 6 carbon atoms, a cycloalkyl group, an alkenyl group having 2 to 6 carbon atoms or an alkynyl group having 2 to 6 carbon atoms, or salts thereof.

Specific meanings of R include n-(or iso-) propyl, n- (iso-,sec- or tert.-) butyl and n- (sec-, neo- or tert.-) pentyl, cyclopentyl, cyclohexyl, cycloheptyl, vinyl, allyl, 1- (or 2-) methyl-2-propenyl and 2-butenyl and 1- (or 2-) propynyl.

The invention also provides novel compositions for combatting insects and acarids comprising carriers, identified more fully hereinbelow, and effective amounts of compounds of the formula

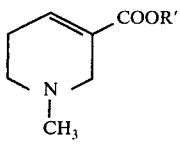

(II)

wherein R' stands for an alkyl group having 2 to 6 carbon atoms, a cycloalkyl group, an alkenyl group having 2 to 6 carbon atoms or an alkynyl group having 2 to 6 carbon atoms.

The invention also provides a process for the production of a compound of formula (I) in which
(a) a compound of the formula

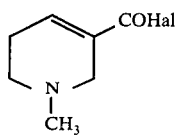

(III)

is reacted with a compound of the formula

R OH (IV)

or
(b) a compound of the formula

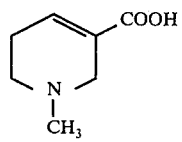

(V)

(which may be in the form of the hydrochloride, hydrobromide or hydrosulfate) is reacted with a compound of the formula

R OH (IV)

with elimination of a molecule of water, or
(c) a pyridinium compound of the general formula

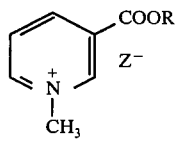

(VI)

(where Z in an anion, for example halide or methylsulfate) is reacted with an agent such as sodium borohydride, or
(d) a compound of the formula

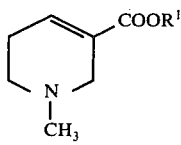

(VII)

(which may be in the form of the hydrochloride, hydrobromide or hydrosulfate) is reacted with a compound of the formula

R OH (IV)

or
(e) a compound of the formula

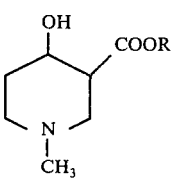

(VIII)

is reacted with a dehydroxylating agent, or
(f) a compound of the formula

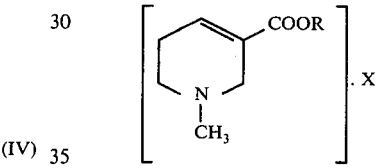

is reacted with an inorganic or organic base, or
(g) a compound of the formula

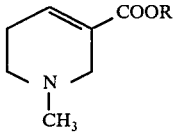

is reacted with an inorganic or organic acid.
In the above formulas (III)–(VII),
R has the same meaning as in formula (I), Hal stands for halogen, for example chlorine or iodine,
R' has the same range of meanings as R or stands for $CH_3$ and
X stands for the hydrochloride, hydrobromide or hydrosulfate.

Examples of the pests which are effected by the present compounds are coleopterous insects, for instance *Sitophilus zeamais, Agriotes fuscicollis* and *Anomala rufocuprea*, lepidopterous insects, for instance *Lymantria dispar, Malacosoma neustria, Pieris rapae, Adoxophyes orana, Homona magnarima* and *Euproctis pseudoconspersa*, hemipterous insects, for instance *Pseudococcus comstocki, Myzus persicae* and *Rhopalosiphum pseudobrassicae*, and acari, for instance *Tetranychus telarius* (Tetranychus vurticae) and *Panonychus citri*.

The various methods of the invention are illustrated below.

Process variant (a)

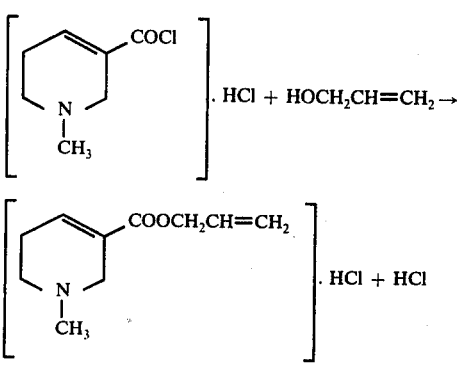

. HCl + HOCH₂CH=CH₂ →

. HCl + HCl

The acylchloride to be used in variant (a) may, for instance, be 1-methyl-1,2,5,6-tetrahydronicotinic acid chloride hydrochloride.

Examples of the alcohols of formula (IV) to be used in this variant (or in variants (b) and (d)) are ethyl, n- (or iso-) propyl, n- (iso-, sec- or tert-) butyl, n- (sec-, neo- or tert-) pentyl, cyclopentyl, cyclohexyl, cyclobutyl-, vinyl-, allyl-, 1- (or 2-) methyl-2-propenyl, 2-butenyl-, and 1- (or 2-) propynyl-alcohol.

The foregoing reaction can be carried out in the presence of an acid binder. Usable as such are hydroxides, carbonates, bicarbonates and alcoholates of alkali metals, and tertiary amines, examples of which include triethylamine, diethylaniline and pyridine.

The above variant (a) can be practiced over a relatively broad temperature range. Generally, a temperature between 0° C and the boiling point of the mixture, and preferably between 30° and 100° C, is used.

The oxychloride for use in the above reaction may be prepared as exemplified by the following formula scheme:

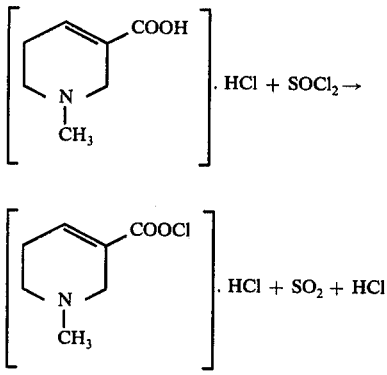

Process variant (b)

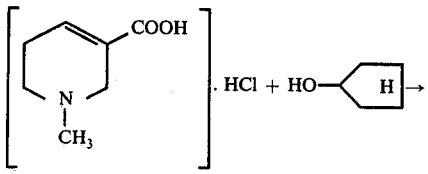

. HCl + HO—⟨H⟩ →

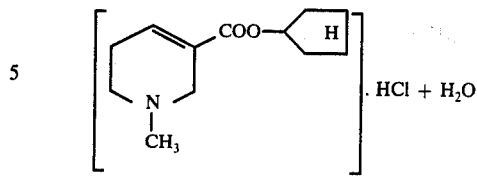

. HCl + H₂O

The carboxylic acid to be used in this process variant may, for example, by a salt (such as hydrochloride, sulfate or bromate) of 1-methyl-1,2,5,6-tetrahydronicotinic acid.

If the above reaction is carried out in the presence of an esterifying agent, for instance, an alkali metal alcoholate or acid such as hydrochloric acid or sulfuric acid, the product of the invention can be obtained in good yields.

The above variant (b) for the preparation of the compounds of this invention can be carried out over a relative broad temperature range. A temperature between 0° C and the boiling point of the mixture, and preferably between 20° and 120° C, is generally used.

Process variant (c)

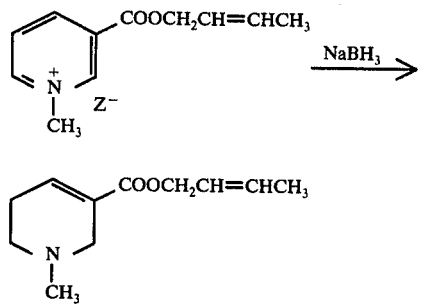

Pyridinium salts to be used in this variant include, for instance, 1-methyl-3-ethoxycarbonyl, 1-methyl-3-n-(or iso-) propoxycarbonyl, 1-methyl-3-n-(iso- or sec-) butoxycarbonyl, 1-methyl-3-n-pentyloxycarbonyl, 1-methyl-3-cyclopentyloxycarbonyl, 1-methyl-3-cyclohexyloxycarbonyl, 1-methyl-3-allyloxycarbonyl, 1-methyl-3-(1'-(or 2')methyl-2'-propenyloxycarbonyl), 1-methyl-3-(2'-butenyloxycarbonyl), and 1-methyl-3-(2'-propynyloxycarbonyl) salts, e.g. pyridinium chlorides, bromides, iodides and methyl sulfates.

As the reducing agent to be used in the reaction, there can be mentioned, for instance, sodium borohydride.

This variant for the preparation of the compounds of this invention can be practiced over a relatively broad temperature range. Generally a temperature between −20° and 50° C, and preferably between −10° and 40° C, is used.

Process variant (d)

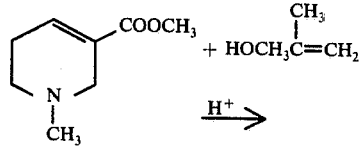

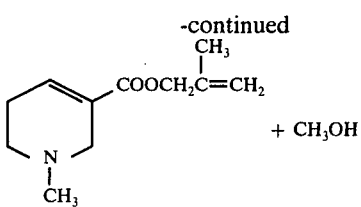

+ CH₃OH

Carboxylic acid esters to be used in this variant include, for instance, 1-methyl-1,2,5,6-tetrahydropyridine-3-carboxylic acid methyl ester, 1-methyl-1,2,5,6-tetrahydropyridine-3-carboxylic acid ethyl ester and their salts; e.g. hydrochlorides or sulfates.

In carrying out the above reaction the use of the esterifying agents indicated for process variant (b) will assist the obtaining of the products in good yields.

This variant can be practiced over a relatively broad temperature range. Generally a temperature between 30° C and the boiling point of the mixture, and preferably between 50° and 100° C, is used.

Process variant (e)

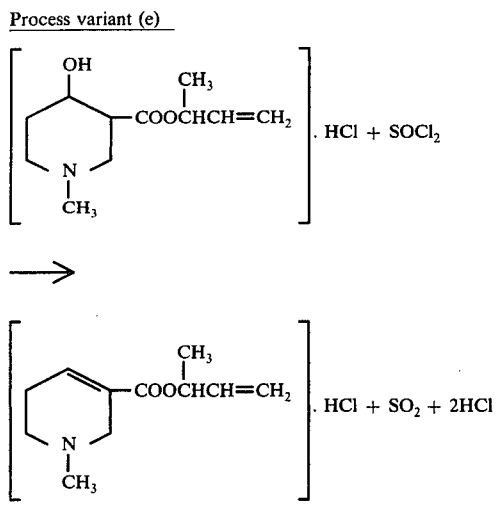

As the 4-hydroxypiperidinium hydrochlorides to be used in the foregoing method for the preparation of the compounds of the invention, mention can be made by way of specific examples, for instance, of 1-methyl-3-ethoxycarbonyl, 1-methyl-3-n-(or iso-) propoxycarbonyl-, 1-methyl-3-n-(iso- or sec-) butoxycarbonyl-, 1-methyl-3-n-pentyloxycarbonyl-, 1-methyl-3-cyclopentyloxycarbonyl-, 1 -methyl-3-cyclohexyloxycarbonyl-, 1-methyl-3-allyloxycarbonyl-, 1-methyl-3-[1'-(or 2'-)methyl-2'-propenyloxycarbonyl]-, 1-methyl-3-(2'-butenyl-oxycarbonyl)- and 1-methyl-3-(2'-propynyloxycarbonyl)-4-hydroxypiperidinium chlorides.

As the dehydrating agent to be used in the reaction can be mentioned, for instance, thionyl chloride and phosphorus oxychloride.

This variant of the process for the preparation of the compounds of the invention can be practiced over a relatively broad temperature range. Generally a temperature between 10° C and the boiling point of the mixture, and preferably between 30° and 50° C, is used.

The tetrahydropyridinium halides which can be obtained by the variants (a), (b), (d) and (e) as described above may be admixed with the same classes of inorganic and organic bases as mentioned for variant (a) to alkalize the solutions from which various corresponding 1-methyl-1,2,5,6-tetrapyridine-3-carboxylic acid esters can be synthesized.

As the acid to be used for the preparation of the salt from the carboxylic acid ester, there may be used an organic or inorganic acid such as HCl, HBr, HI, H₂SO₄, H₃PO₄, HPO₃, HNO₃, HCl₄, HSO₃HN₂, CH₃COOH, Cl₃CCOOH, citric acid, lactic acid, formic acid, oxalic acid, benzoic acid, oleic acid, 2,3,6-trichlorobenzoic acid, dodecylbenzenesulfonic acid, salicyclic acid, —CH₃CCl₂COOH, or any other acid.

The above-mentioned process variants can be carried out using a solvent or diluent. For this purpose any suitable inert chemical or diluent can be used.

Examples of such solvents or diluents include water; aliphatic, cycloaliphatic and aromatic hydrocarbons which may be chlorinated, such as hexane, cyclohexane, petroleum ether, ligroin, benzene, toluene, xylene, methylene chloride, chloroform, carbon tetrachloride, ethylene chlorides, trichloroethylene and chlorobenzene; ethers such as diethyl ether, methyl ethyl ether, di-iso-propyl ether, dibutyl ether, propylene oxide, dioxane and tetrahydrofuran; ketones, such as acetone, methyl ethyl ketone, methyl-iso-propyl ketone and methyl-iso-butyl ketone; nitriles, such as acetonitrile, propionitrile and acrylonitrile; alcohols, such as methanol, ethanol, iso-propanol, butanol and ethylene glycol; esters, such as ethyl acetate and amyl acetate; acid amides, such as dimethyl formamide and dimethyl acetamide; sulfones and sulfoxides, such as dimethyl sulfoxide and sulfolane; and bases, such as pyridine.

The reaction is preferably carried out under atmospheric pressure, but it is also possible to operate under an elevated or reduced pressure.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and-/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–20%, preferably 0.005 to 10% by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The compounds of the invention, may be used mixed with other agricultural chemicals, for instance other insecticides and acaricides, or fungicides, nematocides, anti-virus chemicals, weeding agents, plant growth regulators and attractants (for instance, organic phosphoric acid ester type compounds, carbamate type compounds, dithio (or thiol) carbamate type compounds, organic chlorine type compounds, dinitro type compounds, organic sulfur or metalic compounds, antibiotics, substituted diphenyl ether compounds, urea compounds, triazine compounds) or/and with fertilizers. If they are mixed with cholinecsterase inhibitors, such as organic phosphorus containing insecticides (for example Deipretex, Baysit) and carbamate containing insecticides (for example Sanside, Bassa), they exhibit an excellent synergistic effect.

The compounds or formulations may be applied by any of the methods of application generally employed, such as scattering (for example liquid scattering (spraying), misting, atomizing, dusting, granules scattering, water surface application, pouring); fumigation; soil application (for instance mixing, sprinkling), vaporising, (irrigation); surface application (for example coating, banding, powder coating, covering); immersion; or as bait. They can be applied also by means of the ultra-low volume method; in this method formulations are used containing up to 95% or even 100% of the active compound.

The active compounds are geneally applied to areas of crop cultivation in an amount of 3 to 1,000 grams, preferably 30 to 800 grams, of active ingredient per 10 ares. But for special reasons it is possible and may even be necessary for them to be applied in an amount greater or smaller than this.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combatting or controlling pests, e.g. insects and scarids, which comprises applying to at least one of correspondingly (a) such insects, (b) such scarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the paricular active compound of the invention alone or together with a carrier vehicle as noted above.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular active compounds of the present invention are illustrated, without limitation, by the following examples wherein all parts are by weight unless otherwise expressed:

EXAMPLE 1

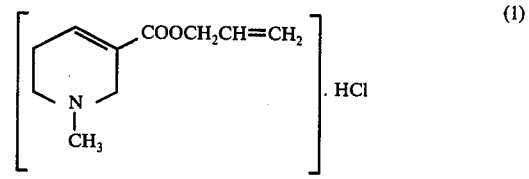

(1)

To 2 grams of 1-methyl-1,2,5,6-tetrahydronicotinic acid hydrochloride were added 16.38 grams of thionyl chloride, and the mixture was stirred at a reaction temperature of 70° C over a period of 10 minutes.

Excess thionyl chloride was removed by means of distillation under reduced pressure to leave 1-methyl-1,2,5,6-tetrahydronicotinic acid chloride-hydrochloride.

To the product obtained above was added 3.4 grams of allyl alcohol and the mixture was left at 27° C for a period of 5 hours, followed by stirring at 90° to 100° C for 2 hours to distil off the unreacted ally alcohol and recrystallizing the residue from chloroform/ether to yield 1.86 grams of the intended product of 1-methyl-3-allyloxycarbonyl-1,2,5,6-tetrahydropyridinium chloride. m.p. 120° – 125° C.

EXAMPLE 2

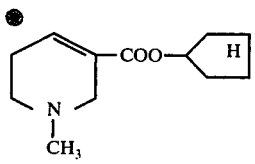
(2)

2 Grams of 1-methyl-1,2,5,6-tetrahydropyridine-3-carboxylic acid hydrochloride were suspended in 6.64 grams of cyclopentanol and dry hydrochloric acid gas was blown into the mixture till the reaction liquid became transparent while stirring of the mixture was being carried out at a reaction temperature of 100° C.

After the completion of the reaction, the excess hydrochloric acid and cyclopentanol were distilled off under reduced pressure, and to the residue was added a 10% aqueous solution of sodium carbonate to render it alkaline, and it was extracted with ether.

The resulting product was dried with anhydrous sodium sulfate and ether was removed by evaporation, and the residue was distilled under reduced pressure to yield 1.31 grams of the intended product of 1-methyl-1,2,5,6-tetrahydropyridine-3-carboxylic aicd cyclopentyl ester.

b.p. 102°–103° C/0.3 mm Hg
$n_D^{20}$ 1.4942.

EXAMPLE 3

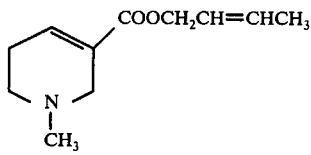

10 Grams of 1-methyl-3-2'-butenyloxycarbonyl-pyridinium iodide were added to 75 milliliters of methanol and 1.44 gram sodium borohydride was added little by little to the mixture at a reaction temperature of 0° C with stirring. The reaction was continued for 40 minutes after the addition.

After the completion of the reaction, methanol was distilled off and 30 milliliters of water were added to the reaction product which was then extracted with ether.

By following the same subsequent procedures as described in Example 2 there were obtained 1.88 gram the intended product 1-methyl-1,2,5,6-tetrahydropyridine-3-carboxylic acid-2'-butenyl ester.

b.p. 96°–97° C/0.4 mm Hg
$n_D^{20}$ 1.4890.

By similar procedures there were prepared the following compounds:

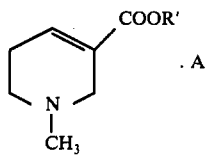

(where A is shown the product was a salt of the indicated acid)

Table 1

| Compound | R' | A | Boiling point, refractive index | Melting point |
|---|---|---|---|---|
| 4 | $C_2H_5-$ | — | 69–70° C/0.6mm Hg $n_D^{20}$ 1.4758 | |
| 5 | $C_2H_5-$ | HCl | | 124–126° C |
| 6 | $n-C_3H_6-$ | — | 73–74° C/0.2 mm Hg $n_D^{20}$ 1.4730 | |
| 7 | $n-C_3H_7-$ | HCl | | 110–112° C |
| 8 | $iso-C_3H_7-$ | — | 75–76° C/0.65 mm Hg $n_D^{20}$ 1.4674 | |
| 9 | $n-C_4H_9-$ | — | 86–88° C/0.5 mm Hg $n_D^{20}$ 1.4730 | |
| 10 | $n-C_4H_9-$ | HCl | | 126–128° C |
| 11 | $iso-C_4H_9-$ | HCl | | |
| 12 | $sec-C_4H_9-$ | — | 83–84° C/0.7 mm Hg $n_D^{20}$ 1.4695 | |
| 13 | $n-C_5H_{11}-$ | — | 100–101° C/0.1 mm Hg | |
| 14 | cyclohexyl | — | 112–113° C/0.6 mm Hg $n_D^{20}$ 1.4934 | |
| 15 | $CH_2=CMCH-$ with $CH_3$ | — | 90–91° C/0.7 mm Hg $n_D^{20}$ 1.4805 | |
| 16 | $CH_2=CCH_2-$ with $CH_3$ | — | 101–103° C/2 mm Hg $n_D^{20}$ 1.4680 | |
| 17 | $CH\equiv CCH_2-$ | — | 93–96° C/1.5 mm Hg $n_D^{20}$ 1.5019 | |
| 18 | $CH\equiv CCH_2-$ | HCl | | 173–175° C |

EXAMPLE 4 (WETTABLE POWDER)

15 Parts of compound 2, 80 parts of a mixture of diatomaceous earth with kaolin (1:5) and 5 parts of the emulsifier Runnox (trade name of a polyoxyethylene alkyl aryl ether made by Toho Chemical Co.) were pulverized and mixed to form a wettable powder. It was diluted with water to a concentration of 0.05% and used to treat pests and/or their habitat.

EXAMPLE 5 (EMULSIFIABLE CONCENTRATE)

30 Parts of compound 17, 30 parts of xylene, 30 parts of Kawakasol (trade name of a product of Kawasaki Chemical Co.) and 10 parts of Solpol (trade name of a polyoxyethylene alkyl phenyl ether made by Toho Chemical Co.) were mixed and stirred together to form an emulsifiable concentrate. It was diluted with water to a concentration of 0.05% and sprayed to treat pests and/or their habitat.

EXAMPLE 6 (DUST)

2 Parts of the compound 15 and 98 parts of a mixture of talc and clay (1:3) were pulverized and mixed together to form dusts. They were applied to pests and/or their habitat.

EXAMPLE 7 (DUST)

1.5 Parts of compound 4, 0.5 part of isopropyl hydrogen phosphate (PAP) and 98 parts of a mixture of talc and clay (1:3) were pulverized and mixed together to make dusts and applied to pests and/or their habitat.

EXAMPLE 8 (GRANULES)

A mixture consisting of 10 parts of compound 1, 10 parts of bentonite, 78 parts of a mixture of talc and clay (1:3) and 2 parts of lignin sulfonate was admixed with 25 parts of water, intimately blended, cut to small pieces by means of an extrusion type granulation machine and made into granules of 20 to 40 mesh in size and dried at 40° to 50° C to prepare granules. They were applied to pests and/or their habitat.

EXAMPLE 9 (GRANULES)

95 Parts of particles of clay having a particle size distribution of 0.2 to 2 mm were placed in a rotary mixer and sprayed, while this was in operation, with 5 parts of compound 18 dissolved in an organic solvent and uniformly moistened, followed by drying at 40° to 50° C to prepare granules. They were applied to pests and/or their habitat.

EXAMPLE 10 (OIL)

0.5 Part of compound 3, 20 parts of Bercicol AR-50 (trade name of a high boiling point aromatic compound sold by Bercicol Co.) and 9.5 parts of kerosene were mixed and stirred together to from an oil. It was applied to treat pests and/or their habitat.

EXAMPLE 11

Test of Effect against Smaller Tea Tortrix and Tea Tussock Moth (Preparation of the Test Solution)

Solvent: xylenol 3 parts by weight
Emulsifier: polyoxyethylene alkyl phenyl ether 1 part by weight In order to make a preparation of the active compound, 1 part by weight of the active compound was mixed with the above-given amount of the solvent containing the above-mentioned emulisifier, and the mixture so obtained was diluted with water to a prescribed concentration.

Tea leaves were immersed in a solution of the active compound diluted with water to a predetermined concentration and the solution was aerated, following which the leaves were each placed in a Petri dish of 9 centimeters diameter, in each of which 10 of the insects (incubated larvae of smaller tea tortrix and 3-age stage larvae of tea tussock moth) were left, and the number of insects killed after 24 hours was counted to calculate the killing ratio as a percentage.

The results of the test are given in Table 2.

Table 2

| | Results of test on Smaller Tea Tortrix and Tea Tussock Moth | | | | | |
|---|---|---|---|---|---|---|
| | Killing ratio (%) | | | | | |
| | Smaller Tea Tortrix Concentration of active ingredient | | | Tea Tussock Moth Concentration of active ingredient | | |
| Compound | 1000 ppm | 200 ppm | 40 ppm | 1000 ppm | 300 ppm | 100 ppm |
| 1 | 100 | 100 | 70 | 100 | 100 | 60 |
| 2 | 100 | 100 | 90 | | | |
| 3 | 100 | 100 | 100 | 100 | 100 | 100 |
| 4 | 100 | 100 | 100 | 100 | 100 | 80 |
| 5 | 100 | 100 | 100 | 100 | 100 | 20 |
| 6 | 100 | 100 | 100 | | | |
| 7 | 100 | 100 | 80 | 100 | 100 | 40 |
| 8 | 100 | 100 | 20 | | | |
| 9 | 100 | 100 | 100 | 100 | 100 | 100 |
| 10 | 100 | 100 | 100 | | | |
| 11 | 100 | 100 | 20 | | | |
| 12 | 100 | 100 | 20 | | | |
| 13 | 100 | 100 | 90 | | | |

Table 2-continued

| | Results of test on Smaller Tea Tortrix and Tea Tussock Moth | | | | | |
|---|---|---|---|---|---|---|
| | Killing ratio (%) | | | | | |
| | Smaller Tea Tortrix Concentration of active ingredient | | | Tea Tussock Moth Concentration of active ingredient | | |
| Compound | 1000 ppm | 200 ppm | 40 ppm | 1000 ppm | 300 ppm | 100 ppm |
| 14 | 100 | 100 | 30 | | | |
| 15 | 100 | 100 | 50 | | | |
| 16 | 100 | 100 | 30 | | | |
| 17 | 100 | 100 | 100 | 100 | 100 | 100 |
| 18 | 100 | 100 | 100 | 100 | 100 | 20 |
| Arecholin hydrochloride (control) | 100 | 20 | 0 | 100 | 40 | 0 |
| Nicotine* sulfate (control, commercially available) | 100 | 20 | 0 | 0 | 0 | 0 |

*Nicotine sulfate: 1-1-methyl-2-3'-pyridinyl-pyrrolidine sulfate

EXAMPLE 12

Test on Effect against *Tetranychus cinabarinus*

A kidney bean seedling planted in a vinyl resin pot of 6 centimeters diameter was inoculated with 50 to 100 *Tetranychus cinabarinus* larvae who had already gained resistance to organic phosphoric acid type acaricides, and one day after the inoculation the compound of the invention which was diluted to a predetermined concentration was applied by means of a spray gun in an amount of 50 cubic centimeters per three pots and the pots were left at room temperature. After three days the number of insects killed was counted to estimate insecticidal index in accordance with the following scale.

3 — 0% of the larvae survive
2 — 5% of the larvae survive
1 — 5 to 50% of the larvae survive
0 — more than 50% of the larvae survive.

The results of the test are shown in Table 3.

Table 3

| | Results of tests on *Tetranychus Cinabarinus* | | |
|---|---|---|---|
| | Insecticidal indices Concentration of active ingredient | | |
| Compound | 3000 ppm | 1000 ppm | 300 ppm |
| 1 | 3 | 3 | 2 |
| 3 | 3 | 3 | 1 |
| 4 | 3 | 3 | 2 |
| 5 | 3 | 3 | 1 |
| 9 | 3 | 3 | 1 |
| 17 | 3 | 3 | 2 |
| 18 | 3 | 3 | 3 |
| Arecholine (Control) | 3 | 1 | 0 |
| Nicotine sulfate (Control, commercially available) | 2 | 1 | 0 |
| Phenkaptone* (Control Commercially available) | 2 | 0 | 0 |

*Phenkaptone 0,0-diethyl-S-(2,5-dichlorophenylthiomethyl) phosphorothiolothionate It will be appreciated that the instant specification and examples are set forth by way of illustration and not limitation, and that various modifications and changes may be made without departing from the spirit and scope of the present invention.

What is claimed is:

1. A method of combating insect or acarid pests which comprises applying to the pests or a habitat thereof an insecticidally or acaricidally effective amount of 1-methyl-3-2'-butenyloxycarbonyl-1,2,5,6-tetrahydropyridine or an acid addition salt thereof.

* * * * *